United States Patent
Callahan et al.

(10) Patent No.: US 6,224,628 B1
(45) Date of Patent: May 1, 2001

(54) HAPTICS FOR AN INTRAOCULAR LENS

(75) Inventors: Wayne B. Callahan, Abingdon, VA (US); J. Scott Callahan, Antioch, TN (US)

(73) Assignee: ThinOptX, Inc., Abingdon, VA (US)

( * ) Notice: Subject to any disclaimer, the term of this patent is extended or adjusted under 35 U.S.C. 154(b) by 0 days.

(21) Appl. No.: 09/296,810

(22) Filed: Apr. 23, 1999

(51) Int. Cl.[7] .................................................. A61F 2/16
(52) U.S. Cl. ........................ 623/6.4; 623/6.43; 623/6.49
(58) Field of Search ................................. 623/6.11, 6.38, 623/6.4, 6.42, 6.43, 6.49, 6.52, 6.54

(56) References Cited

U.S. PATENT DOCUMENTS

| | | |
|---|---|---|
| Re. 33,039 | 8/1989 | Arnott . |
| 4,087,866 | 5/1978 | Choyce et al. . |
| 4,174,543 | 11/1979 | Kelman . |
| 4,254,510 | 3/1981 | Tennant . |
| 4,363,143 | 12/1982 | Callahan . |
| 4,441,217 | 4/1984 | Cozean Jr. . |
| 4,451,938 | 6/1984 | Kelman . |
| 4,480,340 | 11/1984 | Shepard . |
| 4,504,981 | 3/1985 | Walman . |
| 4,536,895 | 8/1985 | Bittner . |
| 4,575,374 | 3/1986 | Anis . |
| 4,581,033 | 4/1986 | Callahan . |
| 4,629,460 | 12/1986 | Dyer . |
| 4,676,792 | 6/1987 | Praeger . |
| 4,701,181 | 10/1987 | Arnott . |
| 4,769,035 | 9/1988 | Kelman . |
| 4,778,464 | 10/1988 | Sergienko et al. . |
| 4,787,902 | 11/1988 | Sheets et al. . |
| 4,872,876 | 10/1989 | Smith . |
| 5,047,052 | 9/1991 | Dubroff . |
| 5,258,025 | 11/1993 | Federov et al. . |
| 5,480,428 | 1/1996 | Federov et al. . |

FOREIGN PATENT DOCUMENTS

2165456  4/1986  (GB) .

*Primary Examiner*—Dinh X. Nguyen
(74) *Attorney, Agent, or Firm*—Waddey & Patterson; Richard S. Myers, Jr.

(57) ABSTRACT

Haptics for an intraocular lens are attached to a flexible, deformable optic which is capable of being rolled for insertion through a small incision in the cornea. The outer periphery of the optic is circular. The haptics include a pair of stems extending radially on diametrically opposite sides of the optic. The stems are rectangular in cross section, having greater width than thickness to permit greater flexibility anterior to posterior than superior to inferior. A flexible support bar is mounted at the end of each stem, each bar being bisected by its stem respectively, and being shaped like an arc concentric with the optic. The support bar has greater depth than width, in order to permit greater flexibility proximally than anteriorly and posteriorly. The haptics have a haptic arm mounted in cantilever fashion at the ends of each support bar, each of the arms terminating in a circular or lobular footplate. The arms have greater width than thickness, and the footplates have a thickness of about fifty microns.

21 Claims, 7 Drawing Sheets

HAPTICS FOR AN INTRAOCULAR LENS

BACKGROUND OF THE INVENTION

1. Field of the Invention

The present invention relates to the field of ophthalmology, and particularly to an improved design for haptics for an intraocular lens ("IOL"), the haptics being suitable for implantation of an appropriate optic in either a phakic or an aphakic eye.

2. Description of the Related Art

Ophthalmologists have been developing the art of implanting an artificial lens in the human eye for many years, both to replace the natural lens which has been removed due to disease (an aphakic eye), and to supplement the natural lens with a corrective lens (a phakic eye).

Various pathologic disease processes can cause deterioration of the natural lens requiring removal of the lens, most notably the opacification of the lens which occurs in cataracts. In the developmental stage, cataracts may be treated by frequent changes of eyeglass prescription. When useful vision is lost, the natural lens is generally removed, either intact or by emulsification. When the lens has been removed, correction is achieved either through spectacles, contact lenses, or an intraocular implant.

Common vision problems include myopia (nearsightedness) hypermetropia (hyperopia or farsightedness) and astigmatism. Traditionally such vision problems have been treated with corrective lenses in spectacles or contact lenses. However, as significant improvements and experience has been gained, the use of intraocular implants using corrective lenses has increased.

Generally, the lens separates the aqueous humor from the vitreous body. The iris separates the region between the cornea or anterior of the eye and the lens into an anterior chamber and a posterior chamber. The lens itself is contained in a membrane known as the capsule or capsular sac. When the lens is removed from the eye, the capsule may also be removed (intracapsular excision), or the anterior portion of the capsule may be remove with the lens leaving the posterior portion of the capsule intact (extracapsular extraction), often leaving small folds or flaps from the anterior portion of the capsule. In an intraocular implant, the artificial or prosthetic lens may be inserted in the anterior chamber, the posterior chamber, or the capsular sac. The artificial lenses are usually fixedly attached within the eye, either by stitching to the iris, or by some supporting means or arms attached to the lens, often in the form of sweeping arms called haptics.

In the late 1970's, several intraocular lenses designed for implant in the anterior chamber were developed by D. Pater Choyce. U.S. Pat. No. 4,087,866, issued May 9, 1978, is an example. The lens features four haptics with feet which support the lens in order to avoid the need for clips or sutures to secure the lens to the iris. The lenses designed by Choyce worked; however, sizing the lens to fit the eye was critical to avoid complications. The lenses were made in lengths from 11.5 mm to 14 mm in 0.5 mm increments, and the thickness of the feet were about 250 microns.

A variety of lenses have been developed by C. D. Kelman. In U.S. Pat. No. 4,174,543, issued Nov. 20, 1979, Kelman taught that although the haptics of many prior art patents provided four point support for the lens, the support structures for the haptics were often linked to the lens body so that the support structure could not deflect freely of the lens body, and is therefore liable to irritate portions of the eye in contact with the support structure (col. 1, lines 48–62). The '543 patent described haptics which included a pair of limbs joined to the lens body by stems so that the limbs would deflect independently, the limbs terminating in contact lobes which have a thickness of 0.2 mm (200 microns).

A variety of other shapes and geometries for the lens supporting elements, or haptics, have been disclosed, including: U.S. Pat. No. 4,254,510, issued Mar. 10, 1981 to J. L. Tennant;, U.S. Pat. No. 4,363,143, issued Dec. 14, 1982 to W. B. Callahan; U.S. Pat. No. 4,480,340, issued Nov. 6, 1984 to D. D. Shepard; U.S. Pat. No. 4,504,981 to G. B. Walman; U.S. Pat. No. 4,536,895, issued Aug. 27, 1985; U.S. Pat. No. 4,575,374, issued Mar. 11, 1986 to T. Bittner; U.S. Pat. No. 4,581,033, issued Apr. 8, 1986 to W. B. Callahan; U.S. Pat. No. 4,629,460, issued Dec. 16, 1986 to R. L. Dyer; U.S. Pat. No. 4,676,792, issued Jun. 30, 1987 to D. Praeger; U.S. Pat. No. 4,701,181, issued Oct. 20, 1987 to E. J. Arnott; U.S. Pat. No. 4,778,464, issued Oct. 18, 1988 to Sergienko, et al.; U.S. Pat. No. 4,787,902, issued Nov. 29, 1988 to Sheets, et al.; U.S. Pat. No. Re. 33,039, issued Aug. 29, 1989 to E. J. Arnott; U.S. Pat. No. 4,872,876, issued Oct. 10, 1989 to J. M. Smith; U.S. Pat. No. 5,047,052, issued Sep. 10, 1991 to S. Dubroff; and U.K. Patent No. 2,165,456, published Apr. 16, 1986.

Despite the advances, there remain problems with intraocular implants which may be ameliorated by the improved haptics and method of releasing the haptics of the present invention inside the bulb of the eye. When an intraocular lens is inserted in the eye, an incision is made in the cornea or sclera. The incision causes the cornea to vary in thickness, leading to an uneven surface which causes astigmatism. The insertion of a rigid lens through the incision, even with compressible haptics, requires an incision large enough to accommodate the rigid lens (at least 6 mm), and carries with it the increased risk of complications, such as infection, laceration of the ocular tissues, and retinal detachment. Deformable intraocular lenses made from polymethylmethacrylate ("PMMA"), polysulfone, silicone or hydrogel may be inserted through a smaller incision, about 4 mm.

It is therefore desirable that the intraocular lens be capable of insertion through a small incision. U.S. Pat. No. 4,451,938, issued to C. D. Kelman, shows an intraocular lens in which the lens body is made in two pieces so that each piece may be inserted through the incision separately and then joined by dowels after insertion in the eye. U.S. Pat. No. 4,769,035, issued Sep. 6, 1988, also to Kelman, discloses a foldable lens which may be inserted through an incision about 3.5 mm in length.

When the intraocular lens is inserted in the anterior chamber of the eye, the feet of the haptics, or lens supporting elements, generally lodge in the scleral sulcus, a depression anterior to the scleral spur where the iris and the ciliary muscle join the sclera in the angle of the anterior chamber. The scleral sulcus is crossed by trabecular tissue in which the spaces of Fontana are located. The anterior chamber of the eye is filled with the aqueous humor, a fluid secreted by the ciliary process, passing from the posterior chamber to the anterior chamber through the pupil, and from the angle of the anterior chamber it passes into the spaces of Fontana to the pectinate villi through which it is filtered into the venous canal of Schlemm. The lens must be positioned so the flow of fluid through the trabecular tissue is not blocked or glaucoma may result.

Since the feet of the haptics rest in the scleral sulcus, the flow of fluid will be blocked where the feet are in contact with the trabecular tissue. It is therefore desirable to decrease the amount of surface area of the haptic foot in contact with the trabecular tissue. At the same time, the haptic feet must have sufficient height to prevent adhesive tissue or synechia from growing around the feet and anchoring them to the iris or cornea The opening of the trabecula is about 200 microns. The haptic feet of conventional intraocular lenses are usually on the order of 175 to 200 microns, effectively blocking the openings in the trabecula wherever the feet are in contact with the tissue. U.S. Pat. Nos. 5,258,025 and 5,480,428, issued Nov. 2, 1993, and Jan. 2, 1996, respectively, to Federov, et al., describes a lens surrounded by a sheet-like "positioner" having projections called "supporting elements either at the four corners of or continuously around the positioner, the supporting elements being 0.3 mm long and 0.01 to 0.05 mm thick (7"a and 7"b of FIG. 3 of the '025 patent, 18 of the '428 patent). However, the lens described by Federov is for implantation in the posterior chamber, the lens of the '428 actually having a length short enough to "float". In addition, the sheet-like nature of the positioner prevents independent deflection the feet in response to forces applied by the eye.

In addition, the lens may place a greater or lesser degree of force on the haptic feet as the lens is compressed, depending upon construction of the lens. Since the amount of pressure for a given surface area is proportional to the force, it is desirable to decrease or distribute the amount of force placed on the haptic feet in order to diminish the force applied by the feet on the trabecular tissue. The present invention achieves this goal by mounting the haptic arms on the ends of a flexible support bar in cantilever fashion, the support bar being offset from the lens body by a stem. Applicant is not aware of any similar haptic design in the prior art.

None of the above inventions and patents, taken either singularly or in combination, is seen to describe the instant invention as claimed. Thus a haptics for an intraocuplar lens solving the aforementioned problems is desired.

SUMMARY OF THE INVENTION

Haptics for an intraocular lens are attached to a flexible, deformable optic which is capable of being rolled for insertion through a small incision in the cornea. The outer periphery of the optic is circular. The haptics include a pair of stems extending radially on diametrically opposite sides of the optic. The stems are rectangular in cross section, having greater width than thickness to permit greater flexibility anterior to posterior than superior to inferior. A flexible support bar is mounted at the end of each stem, each bar being bisected by its stem respectively, and being shaped like an arc concentric with the optic. The support bar has greater depth than width, in order to permit greater flexibility proximally and distally than anteriorly and posteriorly. The haptics have a haptic arm mounted in cantilever fashion at the ends of each support bar, each of the arms terminating in a circular or lobular footplate. The arms have greater width than thickness, and the footplates have a thickness of about fifty microns.

Accordingly, it is a principal object of the invention to provide haptics for an intraocular lens which are independently mounted on a flexible support bar offset from the optic in order to decrease the force applied by the haptic footplates on the tissues of the eye.

It is another object of the invention to provide haptics for an intraocular lens having thin footplates on the order of fifty microns in order to decrease the surface area of the haptics in contact with the tissues of the eye.

It is a further object of the invention to provide haptics for an intraocular lens which provide a better distribution of the compressive forces applied to the haptics in order to decrease pressure on the tissues of the eye.

Still another object of the invention is to provide haptics for an intraocular lens which provide four point support for the lens through haptics with arms which may deflect independently and I which are sufficiently flexible to compress and cooperate with a flexible optic for insertion through a narrow incision in the tissue of the eye.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention relates to a novel design for haptics for an intraocular lens. The haptics are spring-like structures which support the optics of an intraocular lens implant in order to maintain the lens in a relatively fixed position within the eye.

Figure 2:
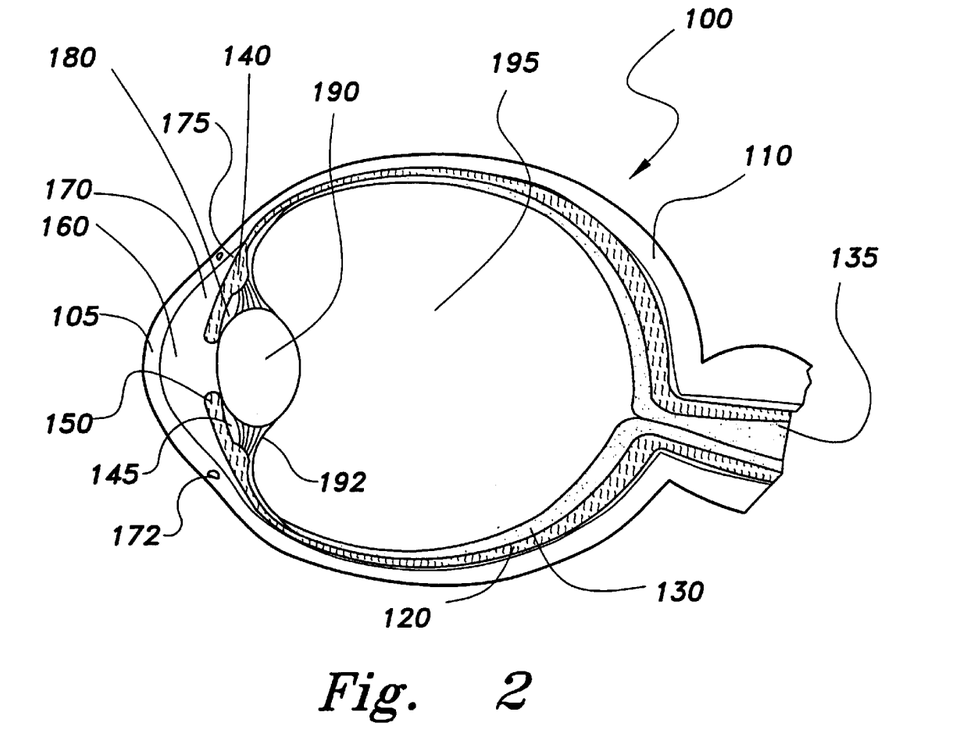
FIG. 2 is a horizontal section view of the human eye.

FIG. 2 is a horizontal section of the bulb of the human eye 100. The eye 100 is coated by three tunics: an outer layer composed of a thick sheath called the sclera 110 covering the posterior ⅚ of the eye, and a transparent covering called the cornea 105 over the anterior ⅙; a middle layer called the choroid 120 posteriorly, containing the vasculature and musculature of the eye, joining the ciliary body 140 and iris 150 anteriorly; and an inner layer called the retina 130, comprising a nervous membrane. The tunics are pierced posteriorly by the optic nerve 135 and blood vessels of the retina.

The iris 150 is an opaque diaphragm having an aperture called the pupil 160 at its center, and expands or contracts the opening of the pupil 160 by contracture and relaxation of the ciliary muscle in the ciliary body 140 to regulate the flow of light into the eye 100. The natural crystalline lens 190 is suspended between the iris 150 anteriorly and the vitreous body 195 posteriorly by ligaments known as the zonules of Zinn 192 attached to the muscles of the eye 100 in the ciliary body 140. At the junction between the iris 150 and the ciliary body 140 is a shallow depression known as the ciliary sulcus 145.

The iris 150 and pupil 160 divide the anterior region of the eye 100 into the anterior chamber 170 and the posterior chamber 180, which are filled with the aqueous humor, a fluid secreted by the ciliary process and flowing from the posterior chamber 180 through the pupil 160 into the anterior chamber 170. At the angle 175 of the anterior chamber 170 (at the junction of the cornea 105, and the iris 150), the fluid is filtered through the spaces of Fontana and the pectinate villi and drains through the sinus venosus sclerae, or canals of Schlemm 172. The lens 190 is contained within a thin membrane called the lens capsule (not shown).

Figure 1:
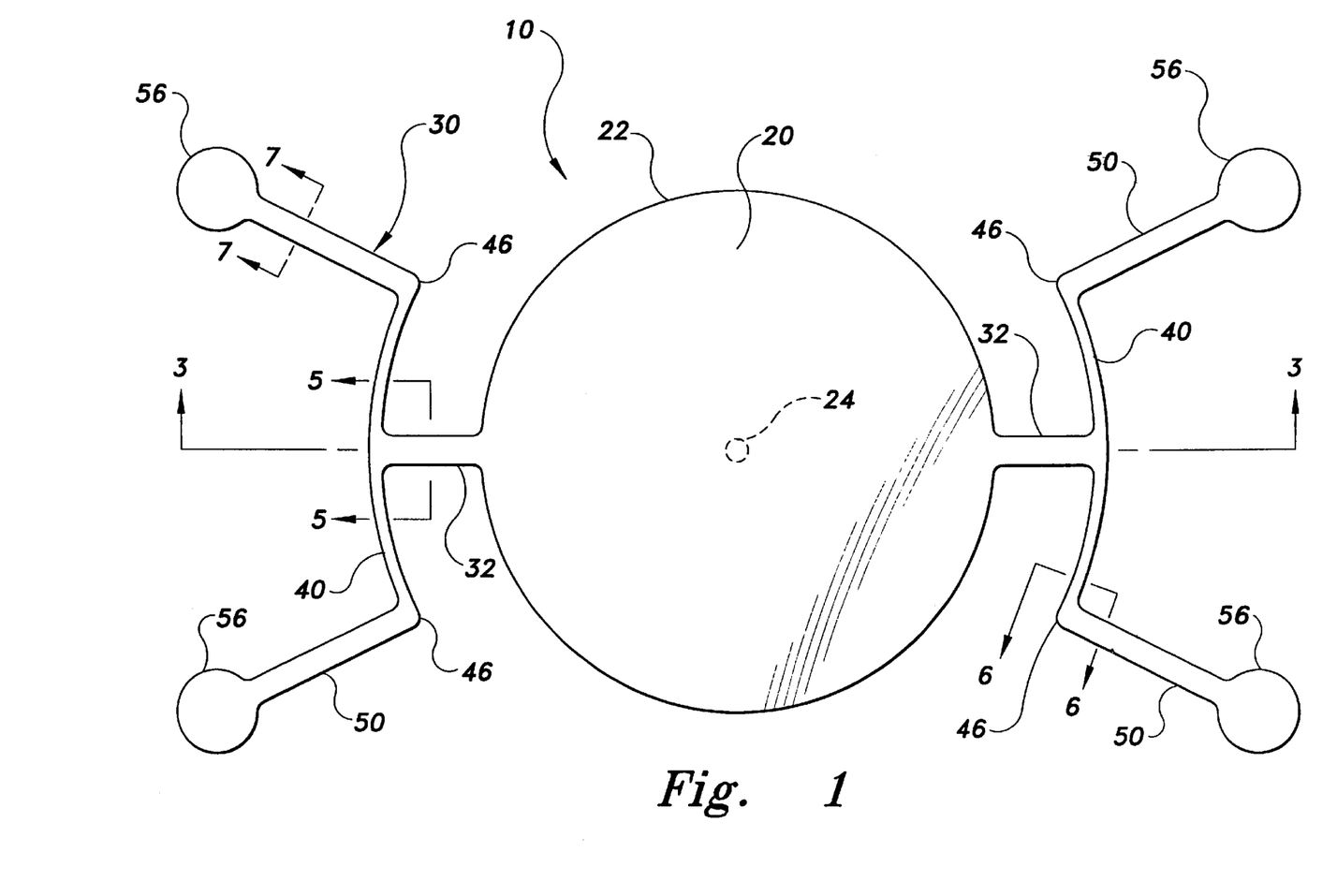
FIG. 1 is a plan view of an intraocular lens for an anterior chamber implant with the haptics for an intraocular lens according to the present invention.

FIG. 1 shows a top view of an intraocular lens, designated generally as 10 in the drawings, for implant into the anterior chamber 170 of the eye 100. A top view of a lens 10 for implant into the posterior chamber 180 would look essentially identical to FIG. 1. The lens 10 comprises a central optical portion referred to as the optic 20. The optic 20 is designed to replace the natural lens in an aphakic eye, or to supplement and correct defects in the natural lens in a phakic eye. The optic 20 will generally be constructed in varying thicknesses, shapes (generally disk shaped, with its outer surfaces biconvex, plano-convex, etc.), and focal powers or properties according to the application.

The haptics 30 of the present invention are designed to be used with optics 20 having different optical properties. The optic 20 and the haptics 30 may be made from different materials, the haptics 30 being joined to the optic 20 by conventionally known methods of fusing plastic materials. However, the haptics 30 are intended for use with and are integral with flexible, resilient, deformable optics 20 made from polymethylmethacrylate ("PMMA"), polysulfone, silicone or hydrogel, preferably PMMA, and are capable of being deformed by compressing, rolling folding, stretching, etc. for insertion into the eye through a small incision, buct being somewhat resilient and having memory characteristics to revert to their original shape when the force producing deformation is removed. In the preferred embodiment, the optic 20 is about 6 mm in diameter and the rim or edge 22 of the optic 20 is about 0.050 mm (50 microns) thick.

The optic 20 may vary in thickness from the center 24 of the optic 20 to the rim 22, depending upon the powers needed in the lenticular surface to provide appropriate corrected vision for the phakic or aphakic patient. Preferably the posterior surface 26 of the lens is provided with a concentric series of annular rings 28, as seen more clearly in FIGS. 3 and 4, of varying thicknesses to produce the desired correction, the outer annular ring 28 on the periphery of the optic 20 having parallel surfaces to correct for edge effects. The posterior surface 26 is preferably concave, having a curvature adapted to conform with the curvature of the iris 150.

Figure 5:
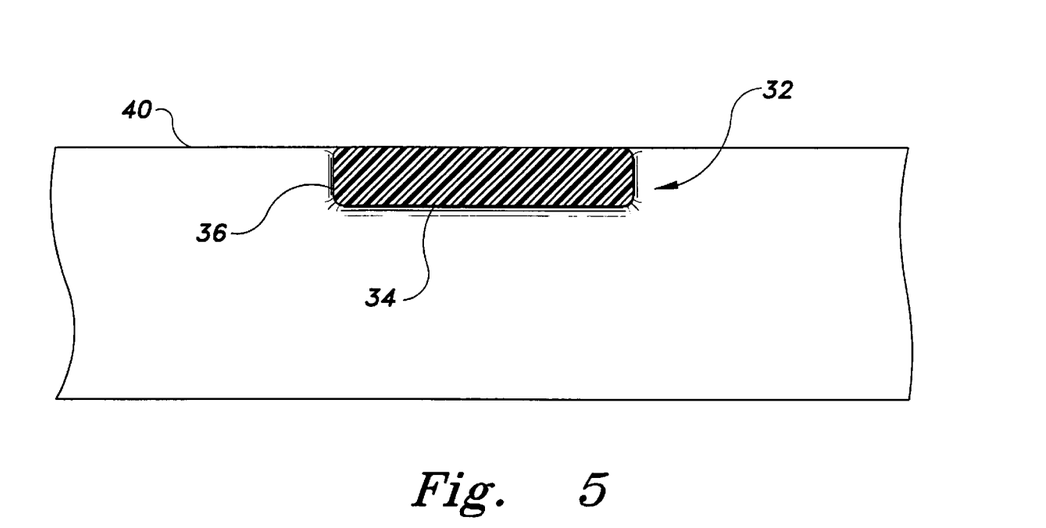
FIG. 5 is a section view along line 5—5 of FIG. 1.

The haptics 30 include a pair of stems 32 extending radially from the edge 22 of the optic 20 on diametrically opposed sides of the optic 20, the stems 32 being disposed in a substantially horizontal plane. As shown more particularly in FIG. 5, the stems 32 are generally rectangular in cross-section, having a width 34 greater than the thickness 36 of the stem 32, the width being measured in a plane substantially perpendicular to a central axis 48 through the center of the optic 20. The width 34 of the stem is preferably about 250 microns, and the thickness of the stem is preferably between about 25 to 100 microns. The thickness of the stems 32 for a lens 10 to be inserted in the anterior chamber 170 are preferably towards the lower end of this range, about 50 microns, in order to permit the stem 32 to bend anteriorly or posteriorly in order to conform to changes in the shape of the eye in response to muscular contractions. The thickness of the stems 32 for a posterior chamber 180 implant may be thicker to add strength to hold the posterior of the capsule in position. The dimensions of the width 34 and thickness 36 of the stem 32 render the stem 32 more flexible superiorly and inferiorly than anteriorly and posteriorly, in order to prevent the lens 10 from contacting the cornea 105 or the iris 150 as the iris 150 contracts and expands according to changing light conditions. The stems 32 extend radially from the optic 20 with the same curvature as the optic 20.

Figure 6:
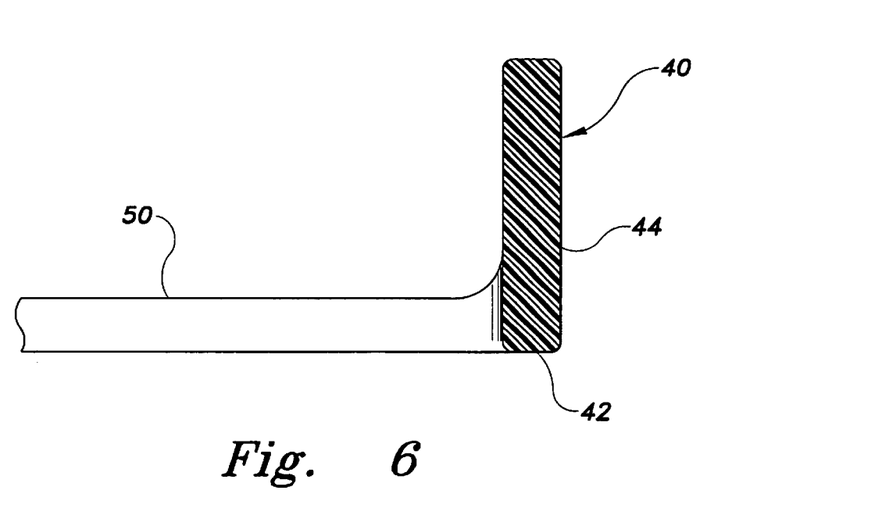
FIG. 6 is a section view along the line 6—6 of FIG. 1.
Figure 7:
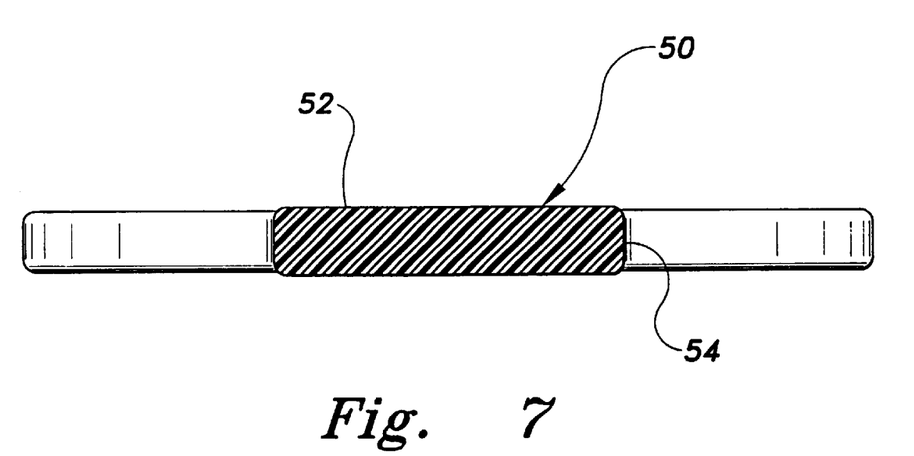
FIG. 7 is a section view along the line 7—7 of FIG. 1.

The haptics 30 include a pair of crossbars 40 attached to the ends of each stem 32 respectively. The crossbar 40 is attached to the stem 32 at the middle of the crossbar 40, so that the stem 32 bisects the crossbar 40. As shown more particularly in FIG. 6, the crossbar 40 is generally rectangular in cross-section, the width 42 being less than the depth 44 of the crossbar 40, the depth 14 being measured in a plane substantially parallel to a central axis through the center of the optic 20. The relative dimensions of the width 42 and depth 44 provide the opposing ends 46 of the crossbars 40 with greater flexibility proximally and distally than anteriorly and posteriorly. In the preferred embodiment, the width 42 of the crossbars 40 is between about 25 and 100 microns, and the depth 44 is about 250 microns. As shown in FIG. 1 the crossbars 40 are arcuately shaped, forming arcs concentric with a central horizontal axis 48 through the center 24 of the optic 20.

Figure 8:
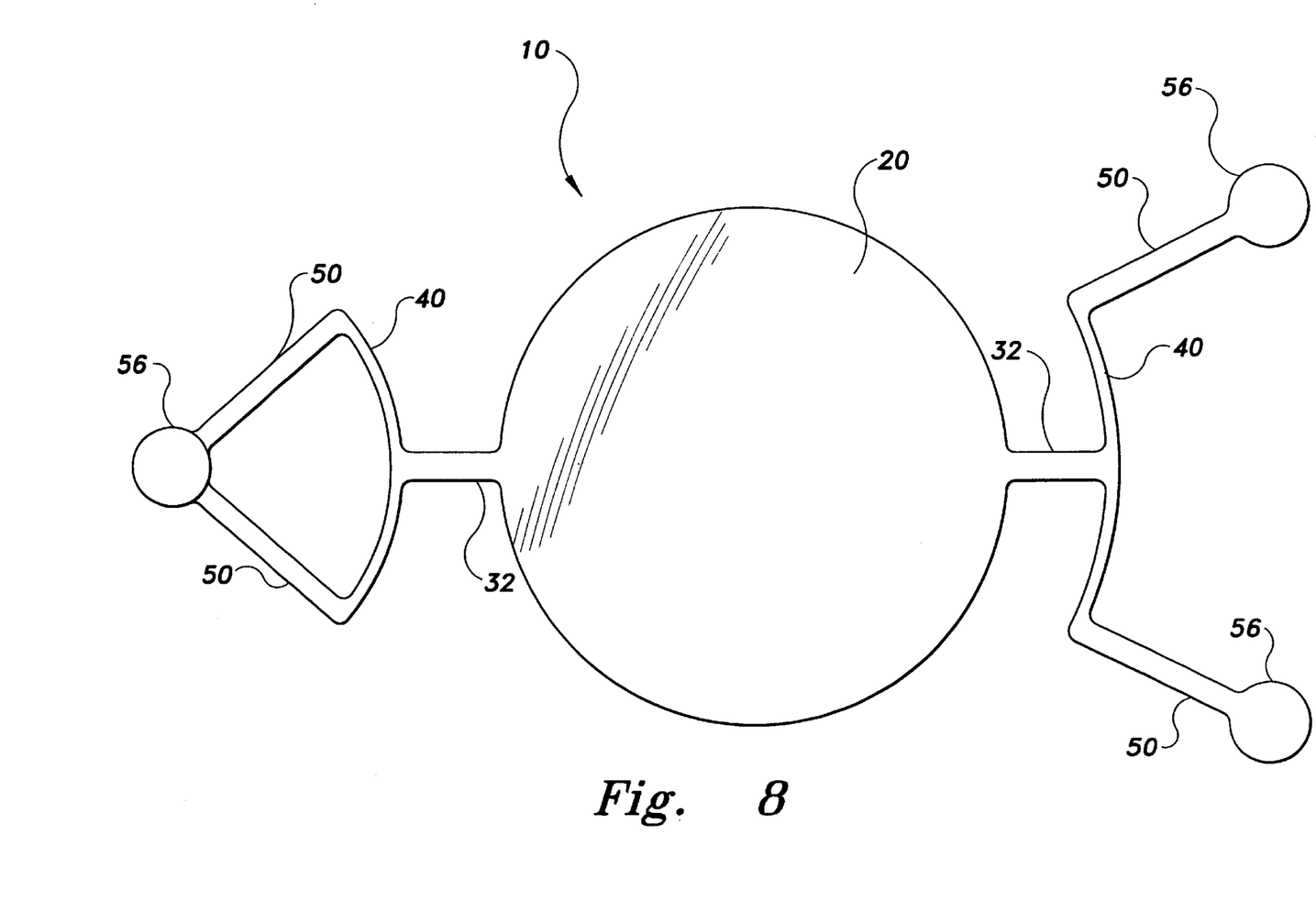
FIG. 8 is a plan view of an intraocular lens with one of the haptics according to the present invention compressed for insertion into the eye.

Each crossbar 40 has a pair of haptic arms 50 attached thereto, the arms 50 being connected at the opposing ends 46 of the crossbar 40 and extending radially therefrom. As shown in FIG. 8, the haptic arms 50 have a cross-sectional shape similar to the stems 32, being substantially rectangular and having a width 52 greater than the thickness 54, the width 52 being measured in a plane substantially perpendicular to a central axis 48 through the center 24 of the optic 20. In the preferred embodiment, the width 52 of the haptic arms 50 is about 250 microns, and the thickness 54 is between about 25 and 100 microns. Each haptic arm 50 terminates in a footplate 56. The footplates 50 are substantially circular or lobular in shape, having the same thickness as the haptic arms 50, preferably about 50 microns. The thin footplates 56 allow clearance when seated in the trabecular tissue of the anterior chamber 170.

Figure 3:
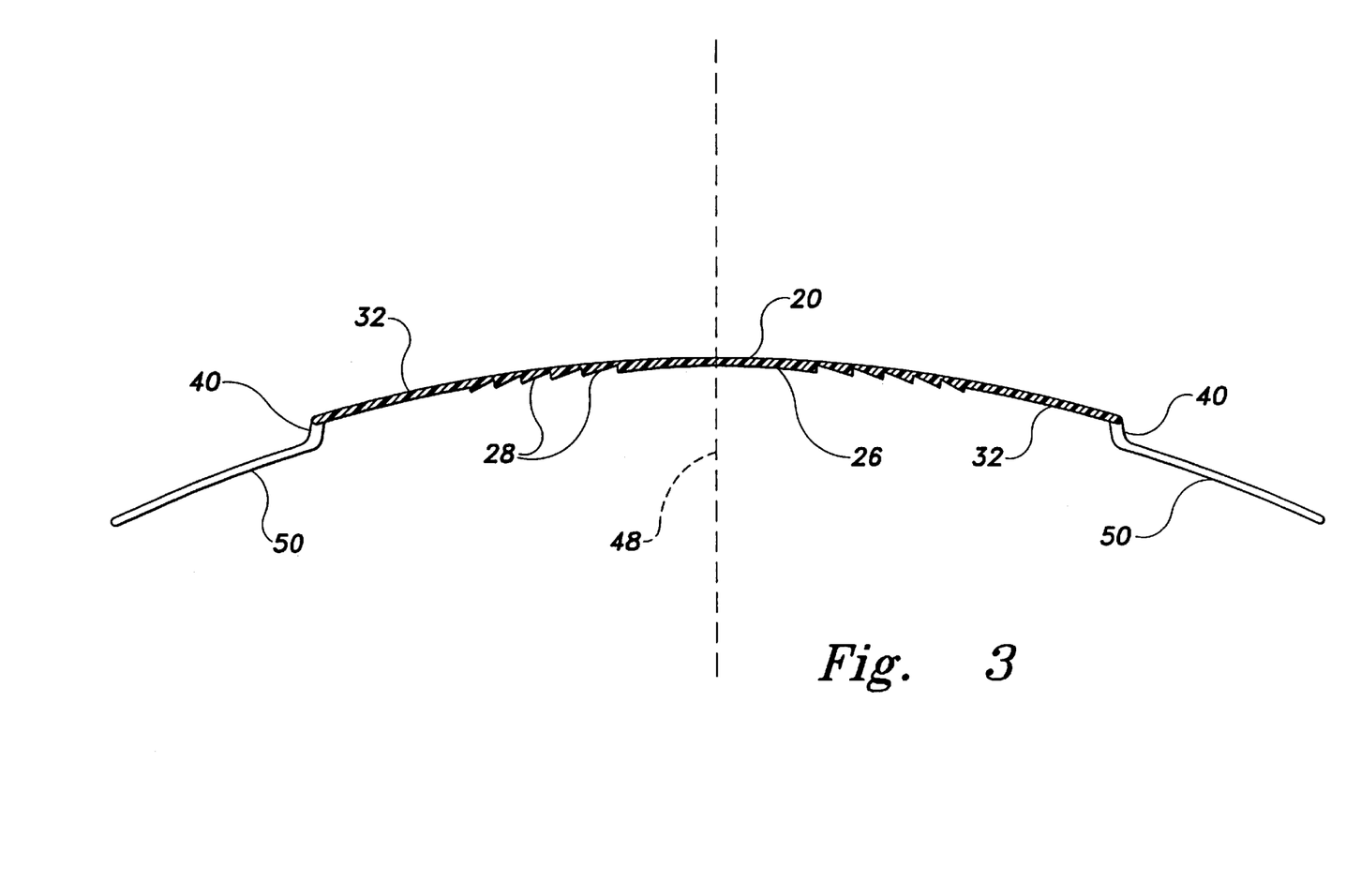
FIG. 3 is a section view along 3—3 of FIG. 1.
Figure 4:
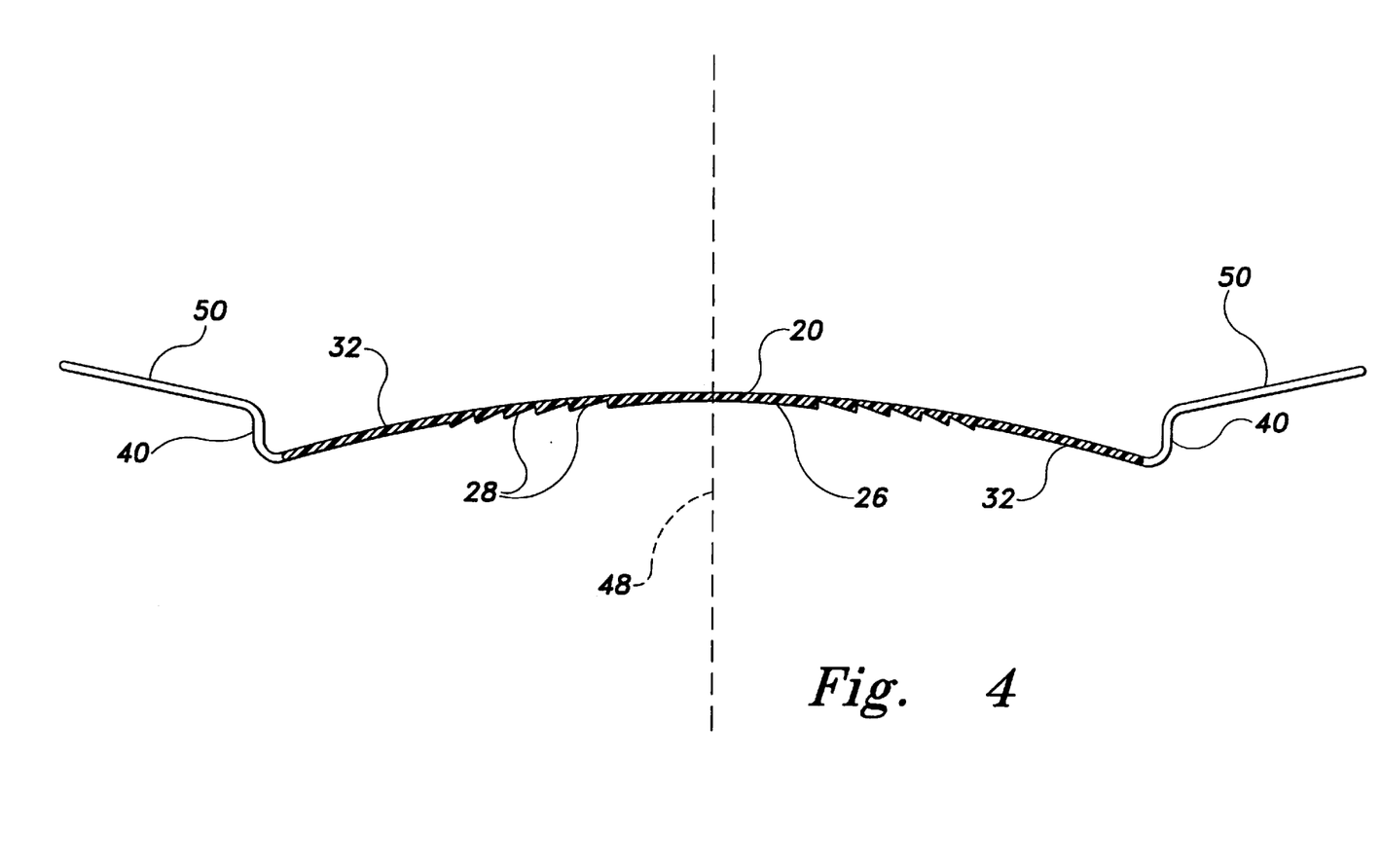
FIG. 4 is a section view of an intraocular lens for a posterior chamber implant with the haptics for an intraocular lens according to the present invention.

The orientation of the haptics 30 depends on whether the lens 10 is for implant into the anterior chamber or the posterior chamber of the eye, as may be illustrated by comparison of FIGS. 3 and 4. FIG. 3 shows an embodiment of the lens 10 for implantation into the anterior chamber 170. In this embodiment, it can be seen that the stems 32 extend radially from the optic 20 with the same curvature as the optic 20, the depth 44 of the crossbars 40 extends posteriorly from the stems 32, and the haptic arms 50 extend radially from the base of the crossbar 40. This configuration has the effect of vaulting the optic 20 forward so that the posterior surface 26 of the optic 20 does not contact the iris 150, while the optic 20 is not vaulted so far forward that it comes into contact with the cornea 105. The haptic arms 50 and footplates 56 have substantially the same radius of curvature as the stems 32, being slightly greater than the radius of curvature of the iris 150.

The embodiment shown in FIG. 4 shows an embodiment of a lens 10 adapted for implantation into the posterior chamber 18C of the eye. In this configuration, the stems 32 extend radially from the toptic 20 with the same curvature as the optic 20. The crossbars 40 extend anteriorly from the stems 32, and the haptic arms 50 extend anteriorly from the ends of the stems 32. The posterior surface 26 of the optic 20 is concave. In this manner the junction between is the stems 32 and the crossbars 40 are positioned posteriorly and the footplates 56 are positioned anteriorly, the lens 10 being avaulted posteriorly, so that the anterior surface of the optic 20 does not contact the iris 150 and so that the posterior surface 26 is slightly anterior to the natural lens 190 in a phakic eye, or so that the rim of the optic 20 stretches the capsular bag in an aphakic eye without adherence of the tissue to the posterior surface 26.

The lens 10 is an integral body, including the optic 20 and the haptics 30, and is preferably made in one piece from PMMA. The optic 20 and the haptics 30 are made with sufficient thinness that the lens 10 is deformable but resilient, having memory so that the optic 20 and haptics 30 return to their unstressed shape when a compressive force is removed. Representative dimensions of the lens 10 include an overall length of about 14 mm from the outermost edge of one footplate 56 to the outermost edge of a diametrically opposed footplate 56. The optic 20 is preferably about 6 mm in diameter. The stems 32 are about 1 mm long, the haptic arms 50 are about 2 mm long, and the footplates 56 have a diameter of about 1 mm.

In use, the surgeon makes a small incision in the cornea 105 or sclera 110. The haptic arms 50 may be compressed, as shown in FIG. 8, so that the footplates 56 of haptic arms 50 connected to the same crossbar 40 overlap in order to fit through the incision, and the optic 20, having thin edges 22, may be rolled for insertion through the incision. Once inserted into the eye 100, the haptics 30 and the optic 20 expand to resume their unstressed shape. Due to the thinness of the haptics of the present invention, the rate at which the lens 10 expands to resume its unstressed shape is much faster than conventionally known lenses, which may take months or years to expand to their unstressed size due to the thickness of conventional haptics. In an anterior chamber 170 implant, the haptic arms expand so that the footplates 56 of the haptic arms 50 seat in the angle 175 of the anterior chamber. In a posterior chamber 180 implant, the footplates 56 may seat in the ciliary sulcus 145 in a phakic eye, or in the capsular bag in an aphakic eye.

Thus, the haptics 30 of the present invention provide support for an intraocular lens 10 which regain their shape faster than conventional lens, and which have fewer complications due to a reduction in the pressure exerted on the tissues of the eye resulting from mounting the haptics on a flexible crossbar 40 and due to the thinness of the haptic arms 50 and footplates 56.

It is to be understood that the present invention is not limited to the embodiments described above, but encompasses any and all embodiments within the scope of the following claims.

What is claimed is:

1. An intraocular lens for insertion into the human eye, comprising:
   a) a lens optic, the optic being substantially disc shaped and having a center, an edge, and a posterior surface;
   b) a first stem and a second stem extending radially from the edge of said optic on diametrically opposed sides of said optic, each of the stems having an end distal to said optic;
   c) a first crossbar attached to the distal end of said first stem and a second crossbar attached to the distal end of said second stem, said crossbars having a depth and a width, wherein said death is greater than said width, and said crossbars being bisected by said stems, and each of said crossbars having opposing ends;
   d) a pair of haptic arms attached to each of said crossbars, each haptic arm extending radially from the opposing ends of said first and second crossbars; and
   e) a plurality of circular footplates, each of said haptic arms terminating in one of the footplates at an end of said haptic arm opposite one of said crossbars;
   f) wherein said intraocular lens is made from a flexible, resilient, deformable material whereby said lens regains its shape after being compressed, bent, folded or stretched.

2. The intraocular lens according to claim 1, wherein each of said stems is substantially rectangular in cross-section, having a width and a thickness, the width being greater than the thickness, the thickness being small enough to permit said stems to flex anteriorly and posteriorly.

3. The intraocular lens according to claim 2, wherein the width of said stems is about 250 microns and the thickness of said stems is between about 25 and 100 microns.

4. The intraocular lens according to claim 1, wherein each of said crossbars is substantially rectangular in cross-section, having a width and a depth, the width being smaller than the depth, the width being small enough to permit the opposing end of said crossbars to flex proximally and distally with respect to said optic, whereby the pressure applied to the eye by said haptic arms and said footplates is reduced.

5. The intraocular lens according to claim 4, wherein the width of said crossbars is between about 25 and 100 microns and the depth of said crossbars is about 250 microns.

6. The intraocular lens according to claim 1, wherein each of said crossbars is arcuately shaped, lying on the circumference of a circle concentric with said optic.

7. The intraocular lens according to claim 1, herein said haptic arms are substantially rectangular in cross-section, having a width and a thickness, the width being greater than the thickness.

8. The intraocular lens according to claim 7, wherein the width of said haptic arms is about 250 microns and the thickness of said haptic arms is between about 25 and 100 microns.

9. The intraocular lens according to claim 1, wherein said footplates have a thickness substantially less than 200 microns.

10. The intraocular lens according to claim 1, wherein said footplates have a thickness of about 50 microns.

11. The intraocular lens according to claim 1, wherein said crossbars have a depth extending posteriorly from said stems, and wherein said haptic arms extend radially from said crossbars, whereby said optic is vaulted anteriorly for insertion into the anterior chamber of the eye.

12. The intraocular lens according to claim 1, herein said crossbars have a depth extending anteriorly from said stems, and wherein said haptic arms extend anteriorly from said crossbars, whereby said optic is vaulted posteriorly for insertion into the posterior chamber of the eye.

13. The intraocular lens according to claim 1, wherein said optic, said stems, said crossbars, said haptics, and said footplates are made as an integral, one-piece body from polymethylmethacrylate.

14. The intraocular lens according to claim 1, wherein said haptic arms are flexible and resilient enough to permit said haptic arms to be compressed towards each other, the footplates of adjacent haptic arms overlapping, in order to insert said intraocular lens through a small incision in a cornea of an eye, said haptic arms returning to their decompressed shape after insertion in order to support said optic in the eye.

15. The intraocular lens according to claim 1, wherein said crossbar is sufficiently thin to permit the opposing ends of said crossbars to flex proximally and distally with respect to said optic, and wherein said haptic arms and said footplates have a thickness less than 100 microns, whereby the pressure exerted on the tissues of an eye by said haptics are reduced.

16. The intraocular lens according to claim 1, wherein said optic has a convex anterior surface and the posterior surface of said optic is concave, said stems having substantially the same radius of curvature as said optic.

17. The intraocular lens according to claim 16, wherein said haptic arms and said footplates have substantially the same radius of curvature as said stems.

18. The intraocular lens according to claim 1, wherein said stems and said haptic arms have a radius of curvature slightly greater than the radius of curvature of an iris of the human eye.

19. Haptics for attachment to a disk-shaped optic of an intraocular lens for insertion into a human eye, comprising:
   a) a first stem and a second stem extending radially from an edge of the optic on diametrically opposed sides of the optic, each of the stems having an end distal to the optic;
   b) a first crossbar attached to the distal end of said first stem and a second crossbar attached to the distal end of said second stem, said crossbars having a depth and a width, wherein said depth is greater than said width, and said crossbars being bisected by said stems, and each of said crossbars having opposing ends;
   c) a pair of haptic arms attached to each of said crossbars, each haptic arm extending radially from the opposing ends of said first and second crossbars; and
   d) a plurality of circular footplates, each of said haptic arms terminating in one of the footplates at an end of said haptic arm opposite one of said crossbars;
   e) wherein said haptics are made from a flexible, resilient, deformable material whereby said haptics may be compressed for insertion into the eye and regain their shape after the compressive force is removed and whereby the opposing ends of said crossbars flex to reduce pressure on the eye.

20. The haptics according to claim 19, wherein:
   a) said stems are substantially rectangular in cross-section, having a width greater than thickness, the width being measured perpendicular to a central axis through the center of the optic, so that said stems may flex anteriorly and posteriorly relative to the optic;
   b) said crossbars are substantially rectangular in cross-section, having a depth greater than width, the depth being measured parallel to a central axis through the center of the optic, so that the opposing ends of said crossbars may flex proximally and distally relative to the optic; and
   c) said haptic arms are substantially rectangular in cross-section, having a width greater than thickness, the width being measured perpendicular to a central axis through the center of the optic, so that said haptic arms may flex anteriorly and posteriorly relative to the optic.

21. A posterior chamber intraocular lens, comprising:
   a) a lens optic;
   b) a first stem and a second stem extending radially from the edge of said optic on diametrically opposed sides of said optic, each of the stems having an end distal to said optic;
   c) a first crossbar attached to the distal end of said first stem and a crossbar attached to the distal end of said second stem, said crossbars having a depth and having a width, wherein said depth is greater than said width, and said crossbars being bisected by said stems, and each of said crossbars having opposing ends;
   d) a pair of haptic arms attached to each of said crossbars, each haptic arm extending radially from the opposing ends of said first and second crossbars; and
   e) a plurality of footplates, each of said haptic arms terminating in one of the footplates at an end of said haptic arm opposite one of said crossbars;
   f) wherein said posterior chamber intraocular lens is deformable and rollable for insertion into the eye, and said lens adequately regains its shape after insertion.

* * * * *